(12) United States Patent
McLoughlin et al.

(10) Patent No.: US 12,403,254 B2
(45) Date of Patent: Sep. 2, 2025

(54) SYSTEM FOR INTERROGATING SERIALLY-CONNECTED DRUG MODULES IN A COMBINATORIAL DRUG DELIVERY DEVICE

(71) Applicant: Bristol-Myers Squibb Company, Princeton, NJ (US)

(72) Inventors: Martin John McLoughlin, Hillsborough, NJ (US); Jeffrey Manfred Gunnarsson, Baltimore, MD (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 782 days.

(21) Appl. No.: 17/771,069

(22) PCT Filed: Nov. 2, 2020

(86) PCT No.: PCT/US2020/058507
§ 371 (c)(1),
(2) Date: Apr. 22, 2022

(87) PCT Pub. No.: WO2021/091814
PCT Pub. Date: May 14, 2021

(65) Prior Publication Data
US 2022/0379024 A1    Dec. 1, 2022

Related U.S. Application Data

(60) Provisional application No. 62/932,791, filed on Nov. 8, 2019.

(51) Int. Cl.
| | | |
|---|---|---|
| *A61M 5/168* | (2006.01) | |
| *A61J 1/20* | (2006.01) | |
| *A61M 5/14* | (2006.01) | |
| *G16H 20/17* | (2018.01) | |

(52) U.S. Cl.
CPC ........ *A61M 5/16827* (2013.01); *A61J 1/2089* (2013.01); *A61M 5/1409* (2013.01); *G16H 20/17* (2018.01); *A61M 2205/50* (2013.01)

(58) Field of Classification Search
None
See application file for complete search history.

(56) References Cited

U.S. PATENT DOCUMENTS

| 4,756,706 A | 7/1988 | Kerns et al. |
|---|---|---|
| 5,807,316 A | 9/1998 | Teeple, Jr. |

(Continued)

FOREIGN PATENT DOCUMENTS

| EP | 0960627 A2 | 12/1999 |
|---|---|---|
| EP | 2930710 A1 | 10/2015 |

(Continued)

OTHER PUBLICATIONS

International Search Report and Written Opinion of the International Searching Authority from PCT International Application No. PCT/US2020/058507, dated Feb. 22, 2021.

*Primary Examiner* — Manuel A Mendez
(74) *Attorney, Agent, or Firm* — Budzyn IP Law, LLC (57) ABSTRACT

In one aspect, a combinatorial drug delivery device is provided herein including: a plurality of serially connectable modules, each including at least one drug component; and, a master controller having a computing processing unit. Each of the modules includes: a non-transitory memory having stored therein an address and an alphanumeric code representative of the at least one drug component contained in the corresponding drug module; a secondary controller operatively linked to the memory of the corresponding module; and, at least one communication bus connectable in series with the communication buses of the modules serially connected with the corresponding module. The master controller is configured to serially interrogate the secondary (Continued)

controllers over the serially-connected communication buses, using the addresses, to request the codes of the corresponding modules. Advantageously, the subject invention provides for a system to confirm the accuracy of drugs provided with the device and the correct sequencing thereof.

10 Claims, 4 Drawing Sheets

(56) References Cited

U.S. PATENT DOCUMENTS

| | | |
|---|---|---|
| 2004/0171985 A1 | 9/2004 | Schubert et al. |
| 2008/0015493 A1 | 1/2008 | Childers et al. |
| 2011/0021978 A1 | 1/2011 | Martin et al. |
| 2012/0179130 A1 | 7/2012 | Barnes et al. |
| 2012/0323208 A1 | 12/2012 | Bochenko et al. |
| 2013/0336814 A1 | 12/2013 | Kamen et al. |
| 2017/0020784 A1 | 1/2017 | Schweiss et al. |
| 2019/0091406 A1 | 3/2019 | Okamura et al. |

FOREIGN PATENT DOCUMENTS

| | | |
|---|---|---|
| JP | 2018519141 A | 7/2018 |
| JP | 2017537700 A | 8/2020 |
| WO | 1993010851 A1 | 6/1993 |
| WO | 2012080481 A1 | 6/2012 |
| WO | 2013102496 A1 | 7/2013 |
| WO | 2016090315 A1 | 6/2016 |
| WO | 2019217820 A1 | 11/2019 |
| WO | 2019217845 A1 | 11/2019 |
| WO | 2019217864 A1 | 11/2019 |

Table 1: Address assignment and Drug ID

| Module 1 (12F) | Module 2 (12E) | Module 3 (12D) | ... | Module 6 (12A) | Master (40) |
|---|---|---|---|---|---|
| Sees that its switch is not actuated; assigns self Address 1. | | | | | Waits |
| Pulses output line 2 times. | | | | | Commands Address 1 to pulse output line 2 times. |
| | Sees input line pulsed 2 times; assigns self Address 2. | | | | Waits |
| | Pulses output line 3 times. | | | | Commands Address 2 to pulse output line 3 times. |
| | | Sees input line pulsed 3 times; assigns self Address 3. | | | Waits |
| | | | ... | | |
| | | | | Sees input line pulsed 6 times; assigns self Address 6. | Waits |
| | | | | Pulses output line 7 times. | Commands Address 6 to pulse output line 7 times. |
| | | | | | Sees input line pulsed 7 times; concludes that all addresses have been assigned. |
| | | | | | Requests drug ID of Address 1. |
| Responds with Drug ID. | | | | | Receives drug ID of Address 1. |
| | | | | | Requests drug ID of Address 2. |
| | Responds with Drug ID. | | | | Receives drug ID of Address 2. |
| | | | | | |
| | | | | Responds with Drug ID. | Receives drug ID of Address 6. |
| | | | | | Now has Drug IDs of all modules. | ental
SYSTEM FOR INTERROGATING SERIALLY-CONNECTED DRUG MODULES IN A COMBINATORIAL DRUG DELIVERY DEVICE

CROSS-REFERENCE TO RELATED APPLICATIONS

This application is a National Stage Application under 35 U.S.C. § 371 of PCT Application No. PCT/US2020/058507, filed Nov. 2, 2020, which claims the priority benefit of U.S. Provisional Application No. 62/932,791, filed Nov. 8, 2019; the contents of which are herein incorporated by reference in their entireties.

BACKGROUND OF THE INVENTION

Combinatorial drug delivery devices and systems are shown and described in: U.S. Provisional Patent Appl. No. 62/670,266, filed May 11, 2018; PCT Appl. No. PCT/US2019/031727, filed May 10, 2019; PCT Appl. No. PCT/US2019/031762, filed May 10, 2019; and, PCT Appl. No. PCT/US2019/031791, filed May 10, 2019. All of the aforementioned patent filings are by the same assignee as herein. As shown in the aforementioned patent filings, drug modules of different liquid drugs may be provided in various combinations to provide different (individualized) drug combinations. The drug modules may be nested, i.e., connected, in series or in parallel, on a tray or other base structure. Alternatively, the drug modules may be serially connected (vertically and/or horizontally) directly to one another. U.S. Provisional Patent Appl. No. 62/670,266, PCT Appl. No. PCT/US2019/031727, PCT Appl. No. PCT/US2019/031762, and, PCT Appl. No. PCT/US2019/031791, are incorporated by reference herein in their respective entireties.

The serially-connected combinatorial system has the advantage in comparison with the nested designs in that it does not require a separate tray component to make the fluid connections and is therefore more efficient in components and, thus, in supply chain.

In the nested system, the tray design can 'store' information on the correct configuration of the modules through the inherent design and layout of the tray design. For example, the tray may provide a configuration (e.g., mechanical cooperating features, such as "lock and key" features) that guarantee only the correct drug modules can be inserted into the nests of the tray and that the correct drug modules are arranged in the correct order. This acts as a safety check in preparing the drug modules for use. In contrast, the serially-connected system does not have a tray-type element and, thus, lacks the ability to have a safety check on this basis.

Because tray-based mechanical means of error prevention are not possible in the serially-connected case, it is desirable to implement other means of detecting configuration errors in the serially-connected system and hence prevent the occurrence of medication errors.

SUMMARY OF THE INVENTION

In one aspect, a combinatorial drug delivery device is provided herein including: a plurality of serially connectable modules, each of the modules including at least one drug component; and, a master controller having a computing processing unit. Each of the modules includes: a non-transitory memory having stored therein an address and an alphanumeric code representative of the at least one drug component contained in the corresponding drug module; a secondary controller operatively linked to the memory of the corresponding module; and, at least one communication bus connectable in series with the communication buses of the modules serially connected with the corresponding module. The master controller is configured to serially interrogate the secondary controllers over the serially-connected communication buses, using the addresses, to request the codes of the corresponding modules. Advantageously, the subject invention provides for a system to confirm the accuracy of drugs provided with the device and the correct sequencing thereof.

In a further aspect, a combinatorial drug delivery device is provided herein including: a plurality of serially connectable modules, each of the modules including at least one drug component; and, a master controller having a computing processing unit. Each of the modules includes: a non-transitory memory having stored therein an alphanumeric code representative of the at least one drug component contained in the corresponding drug module; an actuatable switch having a normally open position, the switch being actuated to a closed position by connecting the corresponding drug module with another of the drug modules; a secondary controller operatively linked to the memory of the corresponding module; and, at least one communication bus connectable in series with the communication buses of the modules serially connected with the corresponding module. With the modules serially connected, each of the secondary controllers determines whether the corresponding switch has been actuated, wherein, upon determining that the corresponding switch has not been actuated, the corresponding secondary controller assigns to the corresponding memory a default address with the default address being transmitted to the master controller. The master controller serially issues commands to the secondary controllers to transmit pulsed signals to adjacent modules, and, wherein, depending on the number of pulsed signals received by the modules, the secondary controllers each assign to the corresponding memory an address with the addresses of the modules being transmitted to the master controller. The master controller is configured to serially interrogate the secondary controller, using the addresses, to request the codes of the corresponding modules.

These and other features of the invention will be better understood through a study of the detailed description and accompanying drawings.

DETAILED DESCRIPTION OF THE INVENTION

Figure 1:
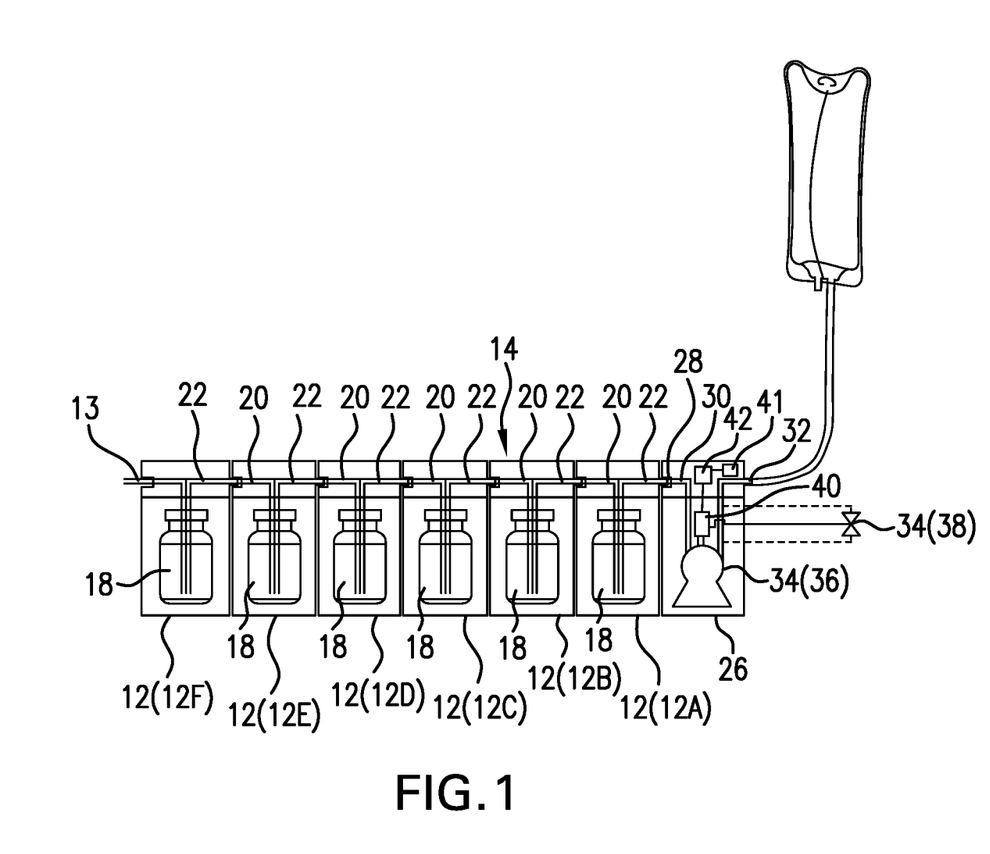
FIGS. 1-6 depict various features of a device formed in accordance with the subject invention.
Figure 2:
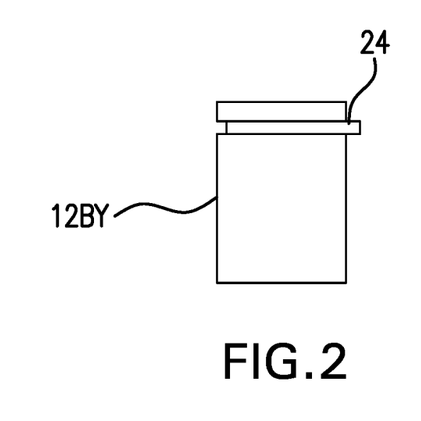
Figure 3:
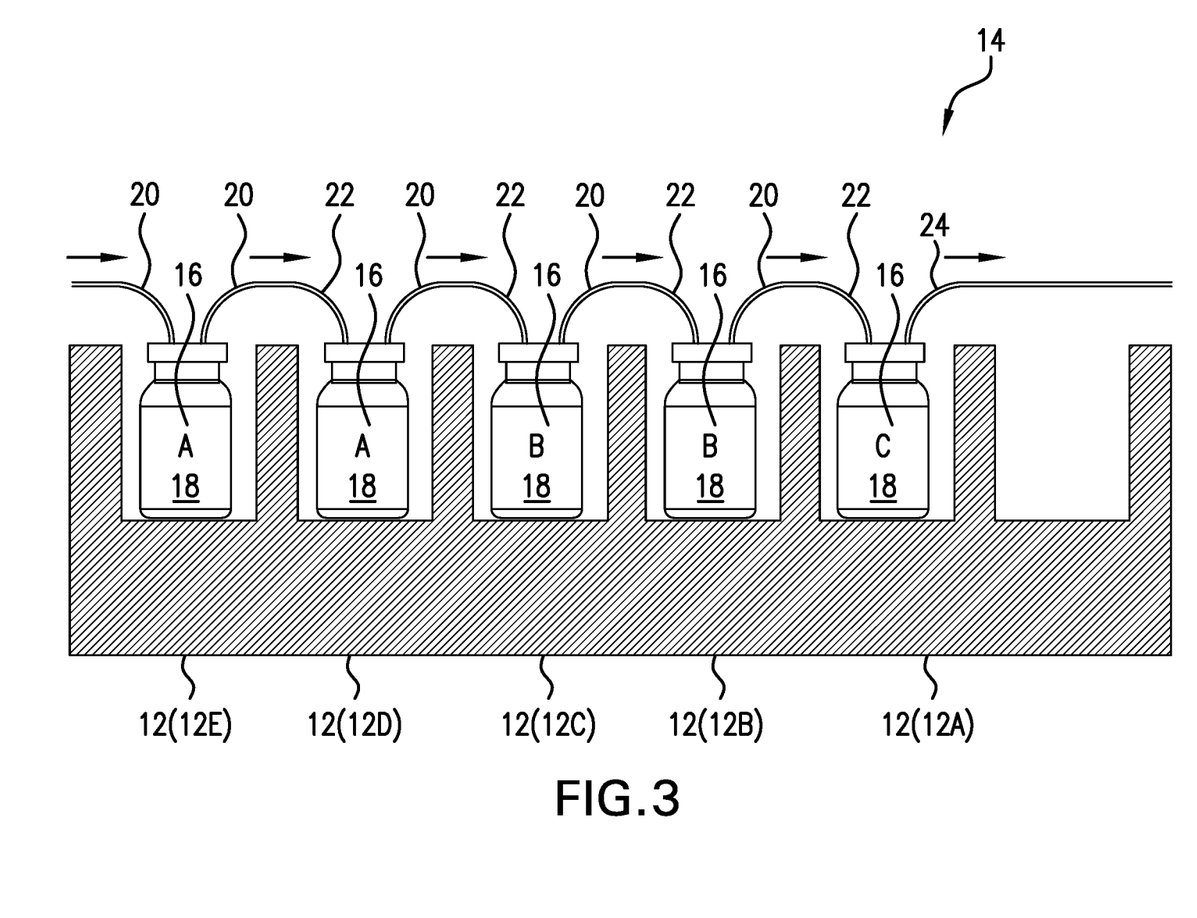

With reference to FIGS. 1-3, an arrangement is shown useable to verify the accuracy of a plurality of serially-connected drug modules 12 of a combinatorial drug delivery device 14. Each of the drug modules 12 includes a drug reservoir 16 for accommodating a liquid drug 18. The drug reservoirs 16 may be defined by portions of the drug modules 12, or be defined by components, such as vials, inserted into the drug modules 12. The combinatorial drug delivery device 14, including any aspect thereof, may be formed in accordance with any of the embodiments disclosed in any of U.S. Provisional Patent Appl. No. 62/670, 266, PCT Appl. No. PCT/US2019/031727, PCT Appl. No.

PCT/US2019/031762, and, PCT Appl. No. PCT/US2019/031791. For illustrative purposes, exemplary features of the combinatorial drug delivery device 14 are described herein. As will be recognized by those skilled in the art, the subject invention is useable with any of the combinatorial drug delivery devices, including being useable with any of the elements thereof (e.g., system 10, drug modules 12, manner of connecting the drug modules 12, flow controller 34, etc.), disclosed in any of the aforementioned patent filings.

As shown in FIG. 1, the drug modules 12 are serially-connected so as to define a single flow path for the drug delivery device 14 through the series of the drug modules 12, through which the liquid drug 18 of each of the drug modules 12 may be drawn. As shown in FIG. 1, inlet and outlet tubing 20, 22, may be provided for each of the drug modules 12 so that the liquid drug 18 may be drawn, in succession, from each of the drug modules 12. As shown in FIG. 3, the inlet and outlet tubing 20, 22 may be formed continuously between the drug reservoirs 16 so that lengths of tubing are provided serving both as an outlet of one of the drug reservoirs 16 and an inlet for the next drug reservoir 16. FIG. 1 shows six of the drug modules 12 (12A-12F). As will be appreciated by those skilled in the art, any quantity of the drug modules 12 may be utilized. A vent 13 may be provided at a terminus of the flow path (in the ultimate drug module).

It is noted that one or more by-pass drug modules 12BY may be needed in a series, to accommodate a place in the series, but to not contain any liquid drug. As shown in FIG. 2, the by-pass drug module 12BY may have by-pass tubing 24 which extends from the inlet to the outlet thereof to allow for flow therethrough without a drug reservoir. Alternatively, as shown in FIG. 3, the by-pass tubing 24 may be provided in lieu of one of the drug modules 12 to connect two components of the drug delivery device 14, such as two of the drug modules 12 or one of the drug modules 12 and the controller housing described below.

The liquid drugs 18 contained in the drug modules 12 may vary in type and concentration. The liquid drug 18 in some of the modules 12 may be a diluent with no pharmaceutically or biologically active agents. The drug modules 12 may contain one or more solid components which can be reconstituted with flow of a diluent therein to form a liquid drug. The ability of the serially-connected drug modules 12 to contain various drug types and concentrations allows for the drug delivery device 14 to be a combinatorial drug delivery device 14, providing for the mixing of various liquid drugs. The liquid drugs 18 intended for a particular combination for a patient is prescribed by a physician. The subject invention provides for the confirmation of accuracy of the inclusion of the particular drug modules 12 in the drug delivery device 14, as well as, the sequence of the drug modules 12. The sequence of the drug modules 14 may be significant, possibly having an impact on the efficacy of the ultimate resulting combination.

The drug delivery device 14 preferably includes a controller housing 26 to which the serially-connected drug modules 12 are connected. The outlet tubing 22 of the first drug module 12A (being the closest to the controller housing 26) is in communication with an inlet 28 formed in the controller housing 26 into which the liquid drug 18 may flow from the drug modules 12. Delivery tubing 30 extends from the inlet 28 to convey the liquid drug 18 through the controller housing 26 to an outlet 32. Tubing or conveyances may be secured to the outlet 32 to direct the liquid drug 18 to a storage device (e.g., an IV bag, injector) or to a drug delivery device connected to a patient (e.g., a butterfly needle).

A flow controller 34 is provided in the controller housing 26 which selectively regulates flow through the delivery tubing 30. In one embodiment, the flow controller 34 may include an actuatable source of negative pressure 36, such as a pump, provided in the controller housing 26 to draw the liquid drug 18 through the inlet 28 and discharge the liquid drug 18 through the outlet 32, via the delivery tubing 30 (which may be discontinuous). In a quiescent state, the source of negative pressure 36 generates no negative pressure, thus, not drawing the liquid drug 18. In a further embodiment, the flow controller 34 may include one or more adjustable valves 38 provided in the controller housing 26 configured to selectively regulate flow through the delivery tubing 30, particularly being configured to be selectively adjusted between open and closed states, such as a ball valve. With the use of the valves 38, a source of negative pressure external to the controller housing 26 may be utilized which is configured to apply negative pressure to the outlet 32 to draw the liquid drug 18 therefrom.

A control unit 40 may be provided in the controller housing 26 which includes a computing processing unit (CPU) 42. It is preferred that the flow controller 34 be electrically powered to be controlled by the CPU 42. For example, an electrical motor or actuator may be provided having a switch configured to be controlled by the CPU 42. Actuation of the motor can cause the source of negative pressure 30 to be activated (e.g., the pump to be turned on), whereas, actuation of the actuator can cause adjustment of the valve(s) 38 to an open state (e.g., rotation of the valve stem to an open state). The switch may be adjusted to an off position by the CPU 42 to turn off the motor, or close the valve(s).

It is envisioned that the drug modules 12 will be serially-connected, when ready for use. Thus, assembly of the drug modules 12 is required by a user, or on behalf of a user. As a fail-safe mechanism, to ensure that the drug modules 12 are properly included in the drug delivery device 14 and in the correct sequence, each of the drug modules 12 may have an alphanumeric code stored therein representative of the drugs 18 contained in the drug modules 12. The alphanumeric codes may designate a drug type and, possibly, a drug's concentration or strength. The liquid drug 18 may be loaded into the drug modules 12 in a manufacturing facility or in a pharmacy with the alphanumeric codes being stored on the modules 12 at the same time. Care is needed to store the correct alphanumeric codes in the drug modules 12.

The specific liquid drugs 18 (type, concentration) will be specified by prescription. The drug modules 12 will be prepared to accommodate the specified liquid drugs 18—the number of the drug modules 12 to be utilized being at least equal to the number of drug components specified by the prescription. The drug modules 12, along with the controller housing 26, may be delivered to the user or a location associated with the user as a kit, for assembly. Instructions will be provided with regards to the assembly of the drug modules 12, including the sequence of the drug modules 12, e.g., first position (closest to the controller housing 26), second position, and so forth.

Figure 4:
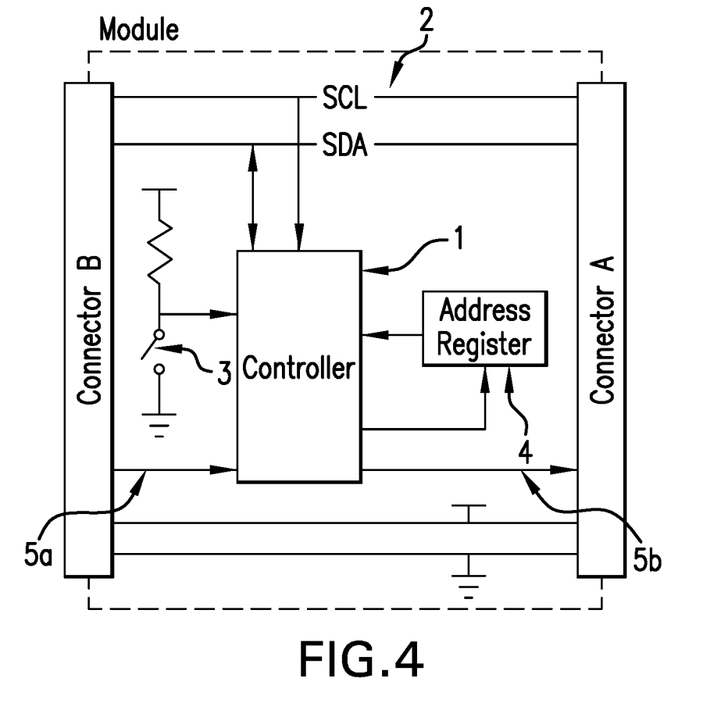
Figure 5:
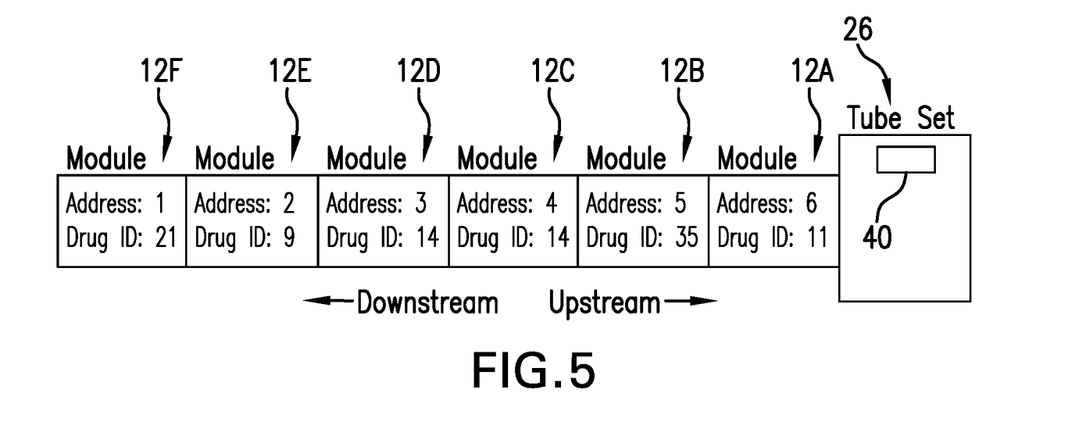

With reference to FIG. 4, a secondary controller 1, which may be a microprocessor or a programmable logic device, is provided for each of the modules 12. The secondary controller 1 may run embedded firmware to implement the logic described below. The secondary controller 1 has access to a compact serial communication bus 2, such as I²C (inter-integrated circuit), as known in embedded electronics. This interface requires two lines: SCL (serial clock) and SDA (serial data). With the modules 12 being serially connected, the communication buses 2 of the modules 12 are serially connected to allow for communication signals to pass between the modules 12. In addition, the communication bus 2 of the first drug module 12A is communicatively coupled with the control unit 40, which acts as a master controller. A non-transitory memory 4, such as an address register or other persistent memory, is operatively linked with the secondary controller 1 of each of the modules 12. The memory 4 may be programmed with a unique address representing a position of the corresponding module 12 (e.g., first position for the module 12A, second position for the module 12B, and so forth). The memory 4 may be used to store the alphanumeric code of the corresponding drugs 18. The unique address may be also stored in the memory 4 at the same time as the alphanumeric code. With the modules 12 being serially connected, as shown in FIG. 5, the control unit 40 may serially interrogate the secondary controllers 1 of the modules 12 over the serially connected communication buses 2, using the unique addresses, to request the stored alphanumeric codes of each of the modules 12. The secondary controllers 1 may transmit the alphanumeric codes, via the serially connected communication buses 2, to the control unit 40. In this way, small volumes of data on the order of a few bytes can be quickly and compactly communicated to the control unit 40. The alphanumeric codes may be placed in sequence to generate an activation code.

The activation code may be used for comparison against an authentication code to determine its accuracy. In one embodiment, the authentication code may be stored in a non-transitory memory 41 associated with the CPU 42 in the controller housing 26. Alternatively, the authentication code may be transmitted to the CPU 42 (e.g., via a receiver on the controller housing 26) with the CPU 42 running a comparison to determine a match. With a match between the activation code and the authentication code, the CPU 42 may actuate the flow controller 34 to enable the delivery of the liquid drug 18.

The flow controller 34 may be provided to have a storage (i.e., non-use) state, e.g., where one or more of the adjustable valves 38 are in closed positions to not permit flow through the delivery tubing 30 to the outlet 32. In addition, or alternatively, in the storage state, the source of negative pressure 36 is in a quiescent state. With a match of the activation code and the authentication code, as described above, the CPU 42 may actuate the flow controller 34, thus causing the flow controller 34 to enter a use state. With the flow controller 34 in a use state, delivery of the liquid drug 18 from the drug delivery device 14 may be achieved. In particular, the one or more adjustable valves 38 may be adjusted to open positions to permit flow through the delivery tubing 30 to the outlet 32. In addition, the source of negative pressure 36 may be actuated, or, alternatively, may be placed into an active state, awaiting actuation (e.g., by a switch on the controller housing 26).

In alternate embodiment, the modules 12 may be configured to self-assign a unique address based on positioning within the device 14. In this embodiment, the modules 12 are not initially provided with an address in the memory 4. To implement this scheme, each of the modules 12 is provided with an actuatable switch 3 (e.g., a mechanical switch) which is preferably normally open. The switches 3 are provided on the modules 12 to be only actuated (i.e., actuated to a closed position) when a module has another module attached to it downstream. In addition, for each of the modules 12, an input line 5*a* is provided, to link with the downstream module 12, that the secondary controller 1 can read, and an output line 5*b* is provided to link with the upstream module 12, that the secondary controller 1 can control.

In this embodiment, with the modules 12 being serially connected, the most downstream module 12 (12F) is the only module that does not have its mechanical switch actuated. The secondary controller 1 on this module 12 therefore concludes that its address should be 1 and assigns itself that address by writing to its memory 4. This address is transmitted to the control unit 40 using the serially connected communication buses 2. The control unit 40, knowing that the module 12 with Address 1 will have automatically assigned itself that address, can then freely communicate with that module over the serially connected communication buses 2.

Figure 6:
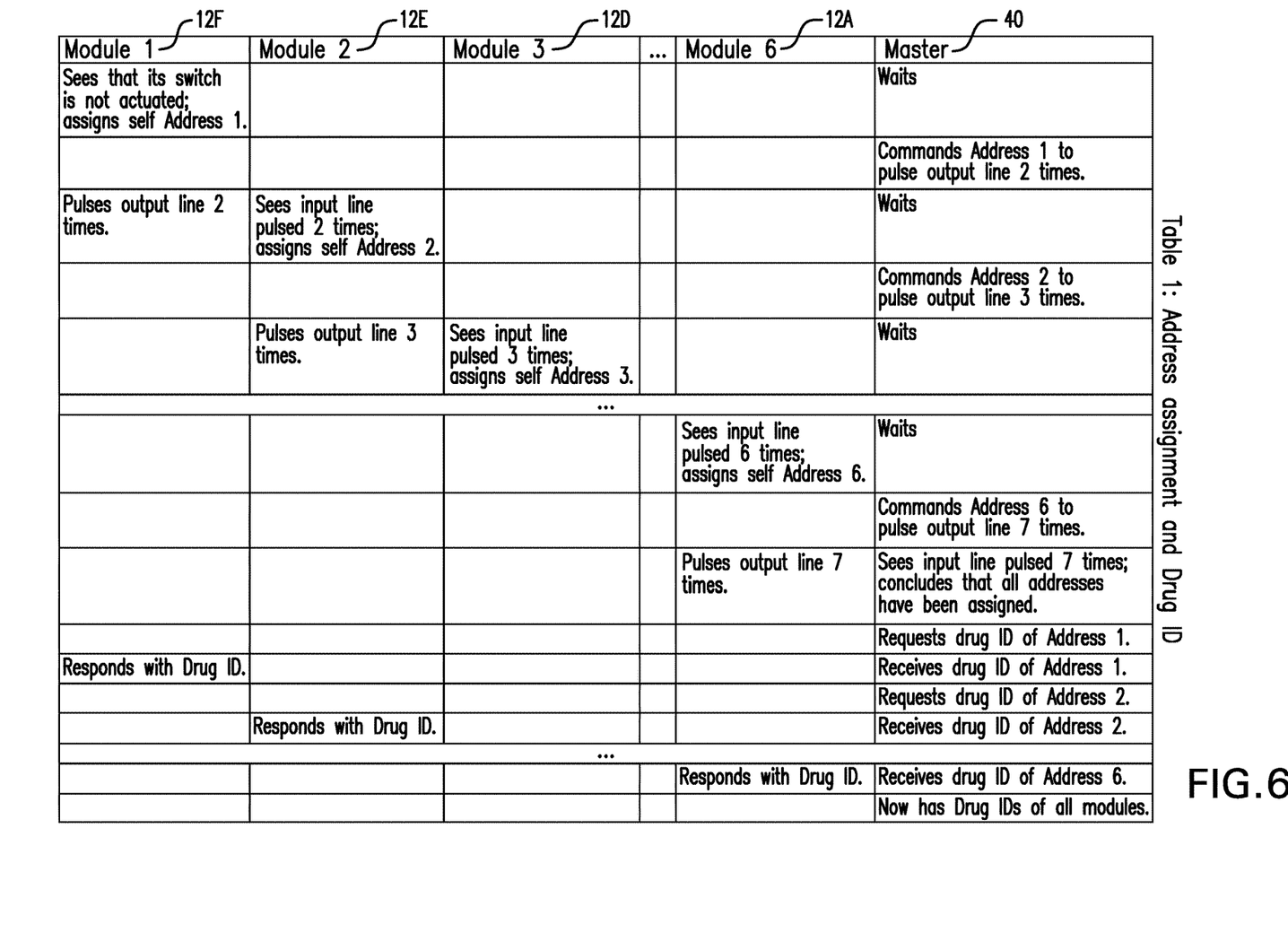

To establish the addresses of the other modules 12, the control unit 40 sends a command to Address 1, i.e., the module 12F, telling it to assert its upstream line 5*b* two times. The module 12F with Address 1 performs this pulsing sequence, which the next upstream module 12E sees by virtue of its input line 5*a*. Because it sees two pulses, the module 12E can conclude that it must be Address 2. The module 12E then writes that address to its memory 4. Subsequently, the control unit 40 knows that Address 2 has been assigned and can freely communicate with that module. So, the control unit 40 issues a command to Address 2, i.e., the module 12E, to pulse its output line 5*b* three times. The next module 12D up sees this pulsing sequence, counting the pulses and concluding that it must be Address 3. This process continues until all addresses have been assigned. Then, the control unit 40 can query each address for its alphanumeric code as explained above. This address assignment protocol is explicated sequentially in FIG. 6.

In one embodiment, any of the combinatorial drug delivery devices disclosed herein is able to deliver two or more drugs for the benefit of the patient suffering from any of a wide range of diseases or conditions, e.g., cancer, autoimmune disorder, inflammatory disorder, cardiovascular disease or fibrotic disorder. In one embodiment, one or more of drug modules 12 may contain a single drug. In one embodiment, one or more of drug module 12 may contain two or more co-formulated drugs. In one embodiment, one or more of drug module 12 may contain a drug in solid form (such as a tablet, capsule, powder, lyophilized, spray dried), which can be reconstituted with flow of a diluent therein to form a liquid drug.

In one embodiment, one or more of the drugs of any of the combinatorial drug delivery devices disclosed herein is an immune checkpoint inhibitor. In certain embodiments, the immune checkpoint inhibitor is Programmed Death-1 ("PD-1") pathway inhibitor, a cytotoxic T-lymphocyte-associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("IDO1") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, any of the combinatorial drug delivery devices disclosed herein includes a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, any of the combinatorial drug delivery devices disclosed herein includes a LAG3 antagonist, e.g., relatlimab or MK-4280, and a PD-1 pathway inhibitor, e.g., nivolumab (OPDIVO) or pembrolizumab (KEYTRUDA). In one embodiment, any of the combinatorial drug delivery devices disclosed herein includes a LAG3 antagonist, e.g., relatlimab or MK-4280, and a CTLA-4 antagonist, e.g., ipilimumab (YERVOY). In one embodiment, any of the combinatorial drug delivery devices disclosed herein includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDO1 antagonist. In another embodiment, the IDO1 antagonist is indoximod (NLG8189; 1-methyl-D-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2',5'-3', 5' cyclic-di-nucleotides; 2'-fluoro substituted, bis-3',5' cyclic-di-nucleotides; 2',2"-diF-Rp,Rp,bis-3',5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In some embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In some embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cergutuzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of any of the combinatorial drug delivery devices disclosed herein is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+ T lymphocyte); CD28CAR/CD137CAR-expressing T lymphocyte; allogeneic CD4+ memory Th1-like T cell s/microparticle-bound anti-CD3/anti-CD28; anti-CD19/CD28/CD3zeta CAR gammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of any of the combinatorial drug delivery devices disclosed herein is an anti-CD73 antibody or antigen binding fragment thereof. In certain embodiments, the anti-CD73 antibody is MEDI9447.

In one embodiment, one or more of the drugs of any of the combinatorial drug delivery devices disclosed herein is a TLR9 agonist. In one embodiment, the TLR9 agonist is agatolimod sodium.

In one embodiment, one or more of the drugs of any of the combinatorial drug delivery devices disclosed herein is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of any of the combinatorial drug delivery devices disclosed herein is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-beta-resistant LMP-specific cytotoxic T-lymphocytes.

In one embodiment, one or more of the drugs of any of the combinatorial drug delivery devices disclosed herein is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of any of the combinatorial drug delivery devices disclosed herein is a SHP-1 antagonist.

In one embodiment, one or more of the drugs of any of the combinatorial drug delivery devices disclosed herein is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of any of the combinatorial drug delivery devices disclosed herein is an agonist of a TNF family member. In some embodiments, the agonist of the TNF family member is ATOR 1016, ABBV-621, or Adalimumab.

In one embodiment, one or more of the drugs of any of the combinatorial drug delivery devices disclosed herein is an Interleukin-2 (IL-2), such as aldesleukin. Preferably, the IL-2 or conjugated IL-2 (e.g., pegylated) has been modified to selectively activate T-effector cells over T-regulatory cells ("T-eff IL-2"), such as bempegaldesleukin. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA). In one embodiment, any of the combinatorial drug delivery devices disclosed herein includes a modified IL-2, such as bempegaldesleukin, which selectively activates T-effector cells over T-regulatory cells, and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a CTLA-4 antagonist, e.g., ipilimumab (YERVOY), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), a CTLA-4 antagonist, e.g., ipilimumab (YERVOY), and a LAG3 antagonist, e.g., relatlimab or MK-4280.

In one embodiment, one or more of the drugs of any of the combinatorial drug delivery devices disclosed herein is a CD160 (NK1) agonist. In certain embodiments, the CD160 (NK1) agonist is an anti-CD160 antibody or antigen binding fragment thereof. In one embodiment, the anti-CD160 antibody is BY55.

In one embodiment, the one or more of drug module 12 may contain a soluble CTLA-4 polypeptide, which can be useful for treating, for instance, T-cell mediated autoimmune disorders, such as rheumatoid arthritis, juvenile idiopathic arthritis, psoriatic arthritis, graft-versus-host disease, and transplant rejection. In one embodiment, the soluble CTLA-4 polypeptide is abatacept (ORENCIA), belatacept (NULOJIX), RG2077, or RG-1046. In certain embodiments, one or more drug modules 12 of a combinatorial drug delivery device as described herein include a soluble CTLA-4 polypeptide, e.g., abatacept (ORENCIA) and a Bruton's tyrosine kinase inhibitor, e.g., branebrutinib. In certain embodiments, one or more drug modules 12 of a combinatorial drug delivery device as described herein include a soluble CTLA-4 polypeptide, e.g., abatacept (ORENCIA) and a tyrosine kinase-2 inhibitor, e.g., BMS-986165. In certain embodiments, one or more drug modules 12 of a combinatorial drug delivery device as described herein include a soluble CTLA-4 polypeptide, e.g., abatacept (ORENCIA) and an Interleukin-2 (IL-2) or "T-reg IL-2", which selectively activates T-regulatory cells as opposed to T-effector cells, e.g., BMS-986326 and NKTR-358.

What is claimed is:
1. A combinatorial drug delivery device comprising:
a plurality of serially connectable modules, each of the modules including at least one drug component, wherein the modules are serially connectable to define a single flow path for the drug delivery device; and,
a master controller having a computing processing unit, wherein, each of the modules includes:
a non-transitory memory having stored therein an address and an alphanumeric code representative of the at least one drug component contained in the corresponding drug module;
a secondary controller operatively linked to the memory of the corresponding module;
at least one communication bus connectable in series with the communication buses of the modules serially connected with the corresponding module, wherein, with the modules being serially connected, the serially-connected communication buses of the modules allow for communication signals to directly pass between the modules,
wherein, the master controller is configured to serially interrogate the secondary controllers over the serially-connected communication buses, using the addresses, to request the codes of the corresponding modules.

2. A combinatorial drug delivery device as in claim 1, wherein the master controller is configured to place the received codes of the corresponding modules in sequence to generate an activation code.

3. A combinatorial drug delivery device as in claim 2, wherein the master controller is configured to compare the generated activation code with an authentication code.

4. A combinatorial drug delivery device as in claim 3, further comprising an actuatable flow controller to selectively regulate flow of the at least one drug component, wherein, the master controller is configured to actuate the flow controller with a match of the generated activation code and the authentication code.

5. A combinatorial drug delivery device as in claim 4, wherein, with actuation, the flow controller causes at least one of: adjustment of one or more adjustable values; actuation of a source of negative pressure; and, placing a source of negative pressure into an active state awaiting actuation.

6. A combinatorial drug delivery device comprising:
a plurality of serially connectable modules, each of the modules including at least one drug component; and,
a master controller having a computing processing unit,
wherein, each of the modules includes:
a non-transitory memory having stored therein an alphanumeric code representative of the at least one drug component contained in the corresponding drug module;
an actuatable switch having a normally open position, the switch being actuated to a closed position by connecting the corresponding drug module with another of the drug modules;
a secondary controller operatively linked to the memory of the corresponding module;
at least one communication bus connectable in series with the communication buses of the modules serially connected with the corresponding module,
wherein, with the modules serially connected, each of the secondary controllers determines whether the corresponding switch has been actuated, wherein, upon determining that the corresponding switch has not been actuated, the corresponding secondary controller assigns to the corresponding memory a default address with the default address being transmitted to the master controller, wherein, the master controller serially issues commands to the secondary controllers to transmit pulsed signals to adjacent modules, and, wherein, depending on the number of pulsed signals received by the modules, the secondary controllers each assign to the corresponding memory an address with the addresses of the modules being transmitted to the master controller,
wherein, the master controller is configured to serially interrogate the secondary controllers, using the addresses, to request the codes of the corresponding modules.

7. A combinatorial drug delivery device as in claim 6, wherein the master controller is configured to place the received codes of the corresponding modules in sequence to generate an activation code.

8. A combinatorial drug delivery device as in claim 7, wherein the master controller is configured to compare the generated activation code with an authentication code.

9. A combinatorial drug delivery device as in claim 8, further comprising an actuatable flow controller to selectively regulate flow of the at least one drug component, wherein, the master controller is configured to actuate the flow controller with a match of the generated activation code and the authentication code.

10. A combinatorial drug delivery device as in claim 9, wherein, with actuation, the flow controller causes at least one of: adjustment of one or more adjustable values; actuation of a source of negative pressure; and, placing a source of negative pressure into an active state awaiting actuation.

* * * * *